United States Patent
Suresh et al.

(10) Patent No.: US 7,263,492 B1
(45) Date of Patent: Aug. 28, 2007

(54) SEQUENCING MODELS OF HEALTHCARE RELATED STATES

(75) Inventors: Nallan C Suresh, Irvine, CA (US); Jean de Traversay, Solana Beach, CA (US); Hyma Gollamudi, San Diego, CA (US); Krassimir G Ianakiev, San Diego, CA (US); Anu K Pathria, La Jolla, CA (US); Michael K Tyler, San Diego, CA (US)

(73) Assignee: Fair Isaac Corporation, San Diego, CA (US)

( * ) Notice: Subject to any disclaimer, the term of this patent is extended or adjusted under 35 U.S.C. 154(b) by 0 days.

(21) Appl. No.: 10/076,961

(22) Filed: Feb. 15, 2002

(51) Int. Cl.
*G06Q 50/00* (2006.01)
(52) U.S. Cl. .............................. 705/2; 705/3
(58) Field of Classification Search ............... 705/2, 705/4, 3; 600/300; 379/114.14; 700/29, 700/30
See application file for complete search history.

(56) References Cited

U.S. PATENT DOCUMENTS

| | | | |
|---|---|---|---|
| 5,253,164 A * | 10/1993 | Holloway et al. | 705/2 |
| 6,223,164 B1 * | 4/2001 | Seare et al. | 705/2 |
| 6,253,186 B1 * | 6/2001 | Pendleton, Jr. | 705/2 |
| 6,529,876 B1 * | 3/2003 | Dart et al. | 705/4 |
| 6,587,552 B1 * | 7/2003 | Zimmermann | 379/114.14 |

FOREIGN PATENT DOCUMENTS

WO    WO 3071388 A2 *   8/2003

OTHER PUBLICATIONS

Wynia et al., Apr. 12, 2000, Physician manipulation of reimbursement rules for patients: Bewteen a rock and a hard place, The Journal of the America Medical Association, vol. 283, Issue 14, p. 1858-1865.*
Welch et al., Sep. 1998, Fraud in the health insurance industry, Journal of the American Society of CLU & ChFC, vol. 52, Issue 5, p. 70-76.*
Hogden, J, 1997, Maximum likehood continunity mapping for fraud detection, p. 1-11.*
Welch et al., Fraud in the health insurance industry, Sep. 1998, Journal of the American Society of CLU & ChFC, vol. 52, Iss. 5, pp. 70-76.*
"HHS/OIG Fiscal Year 2002 Work Plan—Centers for Medicare and Medicaid Services," Department of Health and Human Services, Office of Inspector General, Sep. 2001.

* cited by examiner

*Primary Examiner*—Robert Morgan
(74) *Attorney, Agent, or Firm*—Michael A. Glenn; Robert Sachs; Glenn Patent Group

(57) ABSTRACT

Transition probability sequencing models and metrics are derived from healthcare claims data to identify potentially fraudulent or abusive practices, providers, doctors, clients, or other entities. Healthcare reimbursement claims from hospitals, skilled nursing facilities, doctors, etc., are processed to identify sequences of states, and transition probability metrics are determined from frequency information pertaining to the states. The metrics can these be further analyzed in predictive or rule based models, or other tools.

16 Claims, 3 Drawing Sheets

SEQUENCING MODELS OF HEALTHCARE RELATED STATES

CROSS REFERENCE TO RELATED APPLICATIONS

This application incorporates by reference application Ser. No. 09/606,575, filed on Jun. 28, 2000 entitled "Cascaded Profiles For Multiple Interacting Entities," ("Cascaded Profiles") and application Ser. No. 09/672,142 filed Sep. 27, 2000 entitled "Webstation: Configurable Web-Based Workstation For Reason Driven Data Analysis" ("Webstation").

FIELD OF THE INVENTION

The invention relates to analysis of healthcare reimbursement claims and more particularly to the use of a probability based sequencing model to assist in various healthcare related issues, such as the identification of potentially fraudulent or abusive healthcare providers, the better understanding of the nature of medical services for utilization review and management and disease management. This invention also relates to quality assessment and the impact of the nature of utilization of the various services by providers on healthcare programs such as Medicare and private insurers. While one focus of the descriptions that follow is towards the identification of fraud and abuse, the results derived at any of the various stages in the modeling process described herein may be utilized towards analyses in the other areas mentioned above.

BACKGROUND OF THE INVENTION

Health care fraud continues to be a growing problem in the United States and abroad. According to the Center for Medicare and Medicaid Services (CMS—formerly the Health Care Finance Administration, or HCFA) "fraud is the intentional deception or misrepresentation that an individual knows to be false or does not believe to be true and makes, knowing that the deception could result in some unauthorized benefit to himself/herself or some other person." The CMS states that the most frequent kind of fraud arises from a false statement or misrepresentation made, or caused to be made, that is material to entitlement or payment under the Medicare program. The violator may be a physician or other practitioner, a hospital or other institutional provider, a clinical laboratory or other supplier, an employee of any provider, a billing service, a beneficiary, a Medicare carrier employee or any person in a position to file a claim for Medicare benefits.

Fraud schemes range from those perpetrated by individuals acting alone to broad-based activities by institutions or groups of individuals, sometimes employing sophisticated telemarketing and other promotional techniques to lure consumers into serving as the unwitting tools in the schemes. Seldom do perpetrators target only one sector, public or private, exclusively. Seldom do perpetrators limit fraud schemes to one insurer. Rather, most are found to be defrauding several private and public sector victims, such as Medicare, simultaneously.

According to a 1993 survey by the Health Insurance Association of America of private insurers' health care fraud investigations, overall health care fraud activity broke down as follows:

43% Fraudulent diagnosis
34% Billing for services not rendered
21% Waiver of patient deductibles and co-payments
2% Other In Medicare, the most common forms of fraud includes:

Billing for services not rendered or medically unnecessary
Providing services more often than is medically necessary by Medicare standards, i.e. overutilization
Misrepresenting the diagnosis to justify payment
Soliciting, offering, or receiving a kickback
Unbundling or "exploding" charges
Falsifying certificates of medical necessity, plans of treatment, and medical records to justify payment
Billing for a service not furnished as billed; i.e., upcoding the level of care for higher reimbursement, or routinely provide a higher level of care than is the general standard
Performing "gang visits", e.g. a single visit made to treat a number of people in a nursing home that's billed as multiple individual visits
Referring patients to another provider for services that aren't medically necessary, i.e. "ping-ponging" (typically screening procedures are at fault)
Transferring ("dumping") an uninsured patient (or insured with low reimbursement rates) from one emergency room to another facility in violation of the patient anti-dumping statute.

According to the Center for Medicare and Medicaid Services annual health care expenditures in the United States total nearly $1.1 trillion. The nation's actual 1997 expenditure, for example, totaled $1,092.4 billion. The amount lost to health care fraud and abuse can never be quantified to the dollar. Although estimates of the losses vary widely, a general range may be obtained from literature. For example, in May 1992, citing health insurance industry sources, the US General Accounting Office (GAO) reported to Congress that the loss amounted to as much as 10% of the nation's total annual health care expenditure—or as much as $84 billion in 1992 alone. This high-end estimate of 10% remained common in 2000, at a time when annual US health care spending totaled more than $1 trillion. Many private insurers, for example, when asked their estimates of the proportion of health care dollars lost to fraud, responded with a loss figure ranging from 3-5%, which amounts to roughly $30-$50 billion, annually. In July 1997, based on the first comprehensive audit of Medicare claims paid, the Inspector General of the U.S. Department of Health and Human Services reported to Congress that approximately 14% of Medicare claims dollars—representing some $23 billion—were paid inappropriately, due to fraud, abuse, and lack of medical documentation to support claims. It is widely accepted that losses due to fraud and abuse are an enormous drain on both our public and private healthcare systems.

One of the ways in which fraud can be evaluated, both in the medical care setting and more generally, in any setting involving a transactional relationship is by modeling interactions between different entities such as individuals, organizations or groups. In such cases, the activity related to the problem at hand is largely described by a body of transaction data (historical and/or ongoing) that captures the behaviors of the relevant entities. A few sample settings along with the corresponding transaction data and related entities are described below in Table 1.

TABLE 1

| Problem/Setting | Transactions | Entities |
|---|---|---|
| Healthcare fraud and abuse detection | Claims (inpatient and outpatient) | Client (Patient), Doctor, Hospital, Pharmacy, Lab |
| Credit Card fraud detection | Purchases, Payments, Non-monetary transactions | Account holder, Merchant, Credit Card issuer |
| Bank Checking System | Check processing transactions | Account holder, Bank, Teller |
| Food Stamp fraud detection | Food Stamp transactions | Retailer, Client |

In each of these settings, the common phenomenon is the fact that the encounters between the different entities are captured in the form of the associated transactions.

An entity is an operational unit within a given setting, application or environment and represents objects that interact within that setting, application or environment. The members of an entity are generally objects of a similar type. Different entities interact with each other and their interactions are encapsulated in the transaction data corresponding to that application. Thus, examples of entities in a healthcare setting are clients, providers (this includes doctors, hospitals, pharmacies, etc.), clients' families, etc. and their interactions are captured in the claims data; i.e. the interaction of a healthcare provider and a patient is captured in a claim by the provider for reimbursement. In the credit card world, the interacting entities are account holders, merchants, credit card issuers, and the like and their interactions are captured through different types of transactions such as purchases and payments.

Usually, entities correspond to individuals or organizations that are part of the setting, as the examples in the previous paragraph illustrate. However, more abstract entities characterizing a transaction may also be defined. Examples include procedure codes (describing the type of healthcare service rendered), resource utilization groups (RUG's), diagnosis-related groups (DRG's), and SIC codes (Standard Industry Codes), etc.

The member of an entity is an individual instance of the entity. For example, a specific doctor is a member of the healthcare provider entity, a particular grocery store is a member of the credit card merchant entity and so on.

A target entity is the primary entity of interest for a given application. Usually, it is the focus of some type of analysis such as a statistical model or a rule. A target entity interacts with other entities through the transactions. Thus, in provider fraud and abuse detection, the healthcare providers are the target entity while the clients (patients), clients' families, other providers, etc are the entities interacting with the target entity. In credit card fraud, the merchant would be one example of a target entity (depending upon the type of fraud being analyzed) and the interacting entities then are the cardholder, the credit card issuer, etc. Alternatively, a point of sale terminal could be another type of target entity, and the cashiers who use the terminal would be the interacting entities.

As noted above, a transaction captures the information associated with an interaction between a group of entities. A transaction may initially arise between two entities (e.g. a doctor and a patient) and then be processed by still other entities (e.g. a pharmacy providing a prescription and a laboratory providing a lab test required by the doctor). Different types of transactions will typically capture different types of interactions or interactions between different groups of entities. For example in the credit card setting, a purchase transaction captures the interaction between the cardholder and the merchant, while a payment transaction encapsulates the information regarding the payments made by a cardholder to the credit card issuer. Similarly, in healthcare, an outpatient claim represents the service received by a client (i.e. patient) from a provider as part of an office or home visit, while an inpatient claim encodes data regarding a patient's stay at a hospital or another facility.

In the past, profiles have been created for individual entities and used to develop statistical models based solely on the profiles of the individual entities. For example, U.S. Pat. No. 5,819,226 discloses, among other things, the use of profiles of individual credit card account holders for modeling credit card fraud by such individuals. While this approach is useful for particular applications, in other applications it is desirable to understand the complex interactions between different entities. For example, in order to determine whether there is fraudulent activity by a health care provider, it is important to view the provider's activity not just in a vacuum, but also in relation to the activities of all other providers. Accordingly, profiles based only on transactions of individual members of the entity are insufficient to capture these rich interactions between entities in a manner that yields statistically useful information for modeling the interactions between entities. The ensuing section gives a brief summary of the invention along with the specifics on how the invention captures these interactions between entities.

SUMMARY OF THE INVENTION

We will begin with an exemplary description of the invention. Let us say an event can be identified that involves an object undergoing a chronological sequence of processes (or states) that occur at or may be related to a target entity. In the healthcare context for example a set of procedures is performed by a physician on a client in a sequence for a certain illness; the illness being the event, the client being the object, the procedures being the processes or states and the physician being the target entity. A sequencing model in accordance with the present invention attempts to characterize this sequence by following the object that experiences the sequence and using a metric that captures the rareness of the sequence for the object. This rareness metric is then aggregated to the target entity in some manner, along with the corresponding metrics for all objects that interact with the target entity, which then constitute the target entity's profile, which may be subsequently used as needed, such as in a predictive model.

As related to the issue of healthcare, analyzing this sequence of states encountered by a client and deriving a metric that captures the probability, frequency or rareness of the sequence is one methodology to capture the interaction between multiple entities. In the context of this document a "state" refers to the activity performed by or on the client, and could be for example, the facility or the type of facility the client visits, the procedure performed on the client, the diagnosis, or the drug administered or prescribed to the client. Computationally, a state is a value derived or computed from a set of attributes in the set of data from the entity population, e.g., fields in reimbursement claims data. The derived metric may then be used to determine the aberrance of the client's (or the set of clients') sequence of states and subsequently profile the client or the entities performing or representing these states. Given a set of healthcare reimbursement claims from a group of providers (here, providers may refer to any type of healthcare providers, such as physicians, physician groups, facilities, laboratories, etc.), a model can be built which describes the individual transition probabilities for transitions from one state to another, based on the frequencies of transitions from one state to another by the clients, as evidenced by claims data. Given individual transition probabilities then, the probability of any particular sequence of states, such as that experienced by an individual client can be calculated. The individual sequence probabilities can then be aggregated ("rolled up") from individual clients to particular providers, facilities, or other entities. The development of the underlying model coupled with the rolling-up provides the mechanism for analyzing the interaction between entities.

Let us consider the example of facility-to-facility transition by clients. Here, the healthcare provider is the facility and one example of a state is the facility visited by a client. In this case, the client is "followed" (logically, not physically) across all the facilities or facility types that he/she sees by analyzing the healthcare claims made by these facilities. The sequence of the client's movement is followed from say, a hospital to home to a nursing home, where hospitals and nursing homes are examples of facilities. This "following" identifies the "sequence" of states that the client experiences in one or more episodes of care. A probability for this sequence of states can be then determined from the underlying frequencies of individual state transitions, as contained in model derived from a collection of healthcare data. To the extent that the sequence probability is relatively low, indicating that the sequence is rare, this information can then be used to identify facilities that treated the client and that may be involved in fraudulent schemes or client abuse issues, as described below As noted, information about the sequence of states of many clients can be accumulated to develop probability models that describe the probability of any particular sequence of states for an individual client in one or more episodes of care. Individual sequence probabilities can be processed to determine average or representative sequence probabilities for classes of providers (e.g., peers) as well as individual providers, with respect to any desired client population, such as the set of clients treated by a provider (or who visited a particular facility). This level of aggregated sequence probability information can be used to identify whether the clients of a particular providers or set of providers have unusual (in probabilistic terms) sequences, that is sequences that are unlike state sequences of clients of other providers. For instance, where clients are routinely discharged early, shuttled between two facilities, readmitted soon after discharge due to illnesses stemming from poor quality of care, getting "ping-pong-ed" between consort facilities, or just "dumped" from one ER to another, the two facilities are likely to show distinctive probabilities value which make these sequences appear unusual with respect to other providers. As an other example, when a client rehabilitates in a SNF (skilled nursing facility), one might expect the sequence of RUGs (resource utilization groups), that indicate the level of resources needed for rehabilitation, to progress from more expensive to less expensive RUGs signifying that less intensive resources are required as the client gets well. If the norm for all SNFs seem to dictate this through their sequences, then a SNF may appear aberrant (i.e., potentially fraudulent or abusive) if its clients typically did not switch to less expensive RUGs or even moved to more expensive RUGs during their stay.

Other examples of states may be procedures performed (or illnesses diagnosed) on the client by the provider. Here, the probability of transition from one procedure to another (e.g., a tonsillectomy followed by dialysis) can be determined from the claims data for every pair of procedures. From the individual probabilities the joint probabilities of any particular sequence of procedures on a client may be determined. In this case, the sequence of procedures performed on the client may look aberrant when compared to a norm, the norm being derived from aggregated sequences of other providers or other clients with similar diagnoses. If a doctor is performing procedures in an odd pattern on many of his clients, relative to other doctors treating similar clients, it might indicate that many of the procedures are perhaps not necessary or are incorrectly performed.

The features and advantages described in this summary and the following detailed description are not all-inclusive, and particularly, many additional features and advantages will be apparent to one of ordinary skill in the art in view of the drawings, specification, and claims hereof.

Moreover, it should be noted that the language used in this disclosure has been principally selected for readability and instructional purposes, and may not have been selected to delineate or circumscribe the inventive subject matter, resort to the claims being necessary to determine such inventive subject matter.

These features are not the only features of the invention. In view of the drawings, specification, and claims, many additional features and advantages will be apparent. The specification describes the invention for readability and instructional purposes. It does not limit the invention. A review of the claims is necessary to determine the invention.

The figures depict a preferred embodiment of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE INVENTION

I. System Architecture

Figure 1:
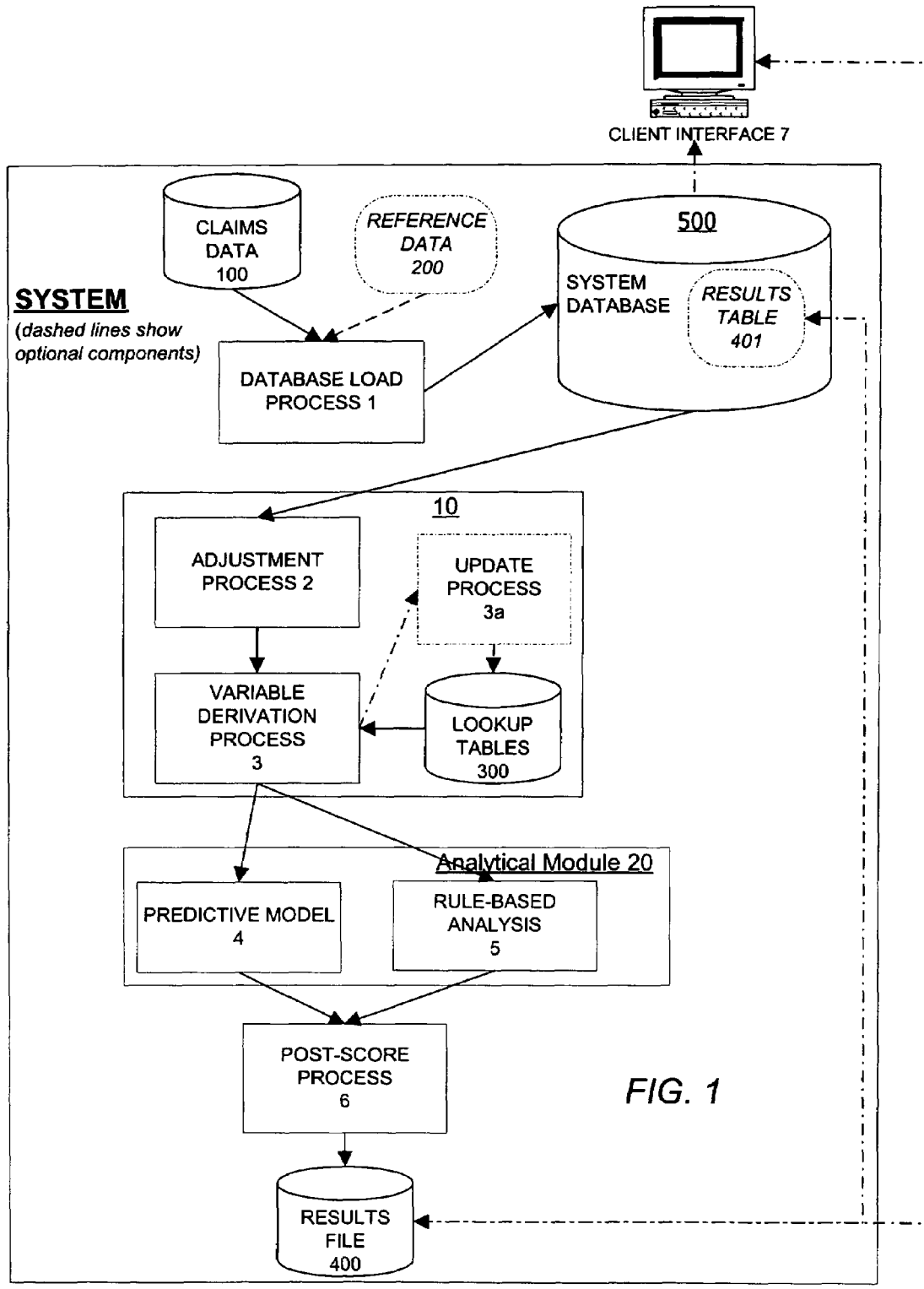
FIG. 1 is an illustration of one embodiment of a system architecture for practicing the invention.

Referring now to FIG. 1 there is shown an embodiment of a system architecture for practicing the present invention.

A claims database 100 usually found in the healthcare line of insurance either follows the professional services standard format (HCFA1500 form), the facilities standard format (UB92 form) or the dental standard format (Dental ADA form). These standard formats are currently (as of the year 2002) being transitioned under HIPAA to new national standards: the ASC X12N 837—Professional, the ASC X12N 837—Institutional, and ASC X12N 837—Dental, respectively. The particular formats and contents for establishing these sequential profiles are expected to vary for different types of insurance (and possibly even for different insurers within the same line of insurance) and are not material to the invention.

The primary data input is claims data for the clients compiled from all available relevant sources. Claims data as used in the invention generally contains information such as claim ID, client ID, date of service, procedure codes, performing physician ID, physician specialty, facility ID (if the claim is from an institution), type of facility, type of disease (diagnosis code or disease category code), payment amount. Supporting data may also be present, which may be specific to the type of state transition considered, be it facility transitions or procedure transitions, or the like. This could be information such as length of qualifying stays, DRG weights, grouping schemes for procedure codes and diagnosis groups, among others.

In order to determine an entity's (such as a client or claimant, as in worker's comp claims) states of interest, claims must contain the relevant field or fields. For example, if the states simply consist in determining which sequence of providers is seeing a client, then the required relevant field would be the provider identification number. If the states focus instead on the sequence of facilities and medical conditions treated in the inpatient hospital environment, the relevant field would then not only be the facility identification number, but also the DRG, which is the diagnosis-related group (DRGs, a relatively broad condition & treatment definition, that determines Medicare's, and other healthcare payers', reimbursement fees). Other fields such as the client identification number and the start- and end-dates of the service are also necessary. The client identification numbers are used to select all of the claims for a given client, and the start- and end-dates are used to sequence the claims, particularly since they are likely to come from different providers/facilities, and to be able to select claims within specific time periods. Often, tables containing descriptor information for the relevant claim fields are loaded separately as reference tables, e.g. the description file for DRGs and their associated MDCs (major disease categories, which essentially represent the higher level groupings of DRGs according to broad physiological systems or types of medical condition).

The claim 100 and supporting reference databases 200 are then be loaded by database load process 1 onto the system database 500, according to predefined input specifications, as would be used for any database loading operation. In order to accommodate all types of operations to handle the revision of a claim after it is first processed, adjustment logic 2 for the required modifications of any claim element gets codified after the load process. The implementation of this logic is a standard/routine procedure and is expected to vary for different types of insurance and for different insurers of the same line of insurance and is not material to the invention.

The system database 500 stores the claims data to be processed and the results 401 of the sequencing modeling. The claims data stored in 500 is the set of claims that go into setting up the profile. The results file 400 and 401 contain the output of the sequencing model. These include transition probabilities matrices, statistics pertaining to the sequence and state information, and any results of predictive modeling 4, rules analysis 5, or scoring 6. The rank ordered list of suspects, the reason codes and values, along with all intermediate computations of profiles for display and to provide supporting documentation for further investigation are all stored in these files.

Profile derivation process 10 performs the bulk of the operations for sequence modeling. The adjustment process 2 properly reconciles all claim adjustment activity incurred by a claim. The variable derivation process 3 analyzes the adjustment-reconciled claims data. The update process 3a first creates the reference transition probabilities across all states; these are then stored in the lookup tables 300. The variable derivation process 3 then uses these reference values to generate the profiles of entities as based on the probabilities of states experienced/associated with these entities. Update process 3a will occur for the initialization of the lookup tables, and then sporadically (i.e. on a monthly, quarterly, or yearly schedule) to refresh the lookup tables.

Analysis module 20 includes predictive model 4 and rules based analysis 5. The predictive model 4 is any type of predictive model (e.g., supervised or unsupervised neural network, logistic regression; discriminant analysis, regression tree, clustering algorithms, etc.) that is trained on the entity profiles incorporating the probability information to predict (classify) entities as potentially fraudulent or abusive. The model can be supervised if known cases of fraudulent providers and their attendant probability profiles are known. If identified examples of fraud are not available in sufficient quality and quantity, then unsupervised (outlier detection) models are preferable to detect unusual occurrences suggestive of inappropriate or illegitimate activity. The rules based analysis 5 is used to identify potentially fraudulent or abusive entities using parametrically defined rules, such as may be defined by an expert in the field of healthcare fraud, abuse or program impact issues. Here the rules would target entities whose probability profiles, sequences, statistics, or other data indicated were likely fraudulent or likely to impact healthcare programs. All outcomes from the analysis module 20 are posted to the results file 400.

II. Functional Operations

Figure 2:
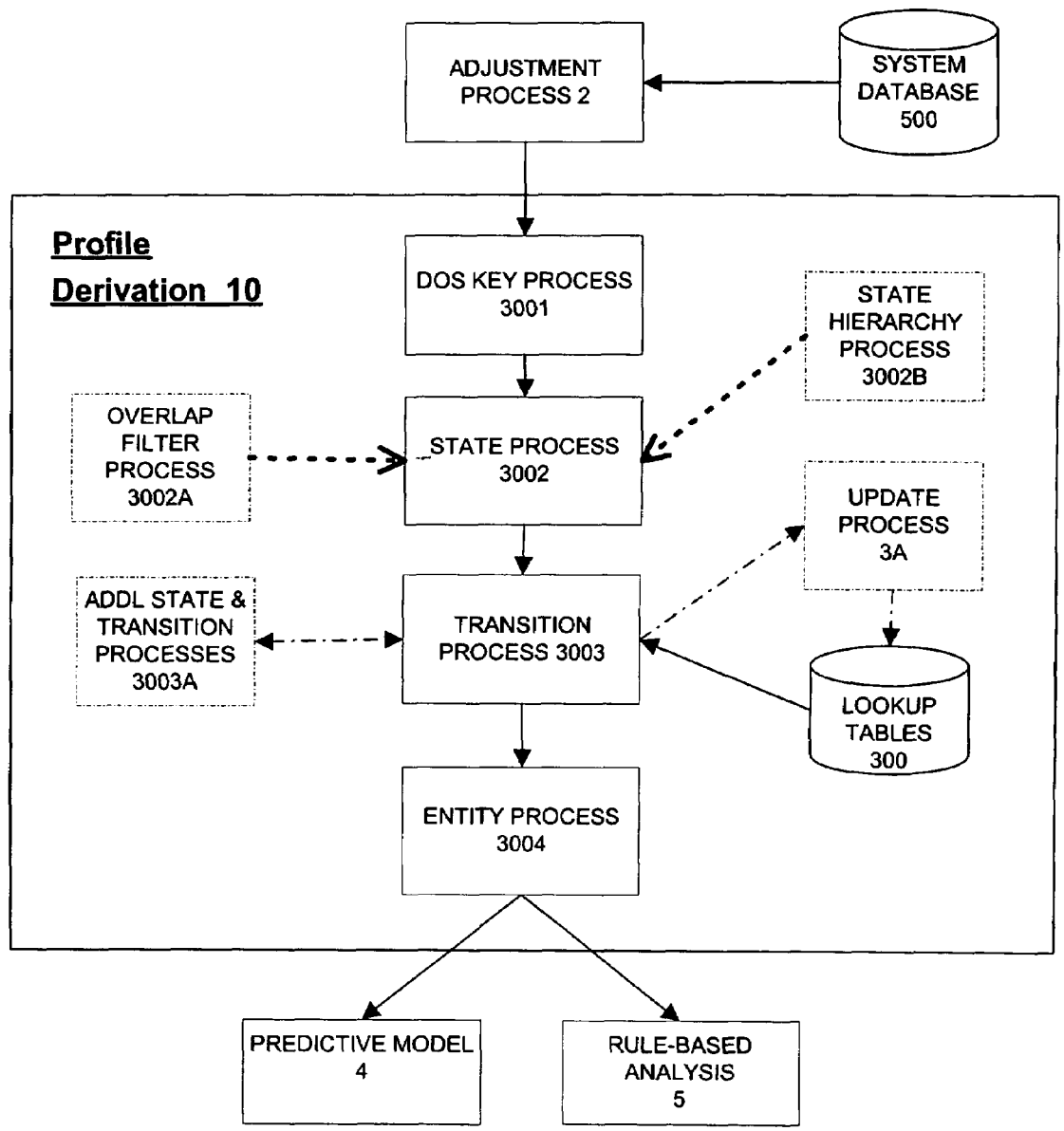
FIG. 2 is a flowgraph of the derivation of sequencing profiles.

Profile derivation 10 is depicted in detail in FIG. 2. Generally, the word "profile" is used to denote a set of behavioral features (profile variables) that figuratively represents the "outline" of an entity. A profile may be understood as a summary of the historical (and/or ongoing) transactional behavior of the entity, which ideally eliminates the need to store the details of all the historical transactions that are summarized by the profile variables. The values of the profile variables can be used to characterize the different members belonging to that entity. The primary intention of a profile is to capture the behavioral characteristics of an entity's members as exhibited through the transactions, in as complete a manner as possible. In the context of this application, a profile of an entity includes a representation of some level of sequence probability information for sequences of states related to the entity. Thus, for healthcare provider entities and where the 'states' are procedures then a profile can describe the aggregated probability of one or more sequences of states across all clients treated by a provider. Or the profile may be the average state transition probability for a particular state transition. Other more complete examples of profiles, states, and the like are described below.

The extent of data processing for profile derivation varies depending on the transition type being analyzed. We will first outline the steps involved in the processing for sequence analysis in the case of client transitions from one facility to another, where the entity being profiled is the facility. The facilities considered are PPS (prospective payment system) inpatient hospitals, non-PPS inpatient hospitals, skilled nursing facilities (SNFs), hospices and home health agencies (HHA), but the method could extended to any choice of facilities. We will then move to a discussion of the more general implementation as illustrated in FIG. 2.

A. Data Processing for Probability Modeling

The first general step towards obtaining the sequences is to collect all the relevant sources of data pertaining to the client, by facility type and for the period of analysis, for example, a year. This is done in order to identify episodes of care, where an episode of care, for this facility transition sequence, refers to a stay at a facility. The data is in the form of claims, with a start and end date. An episode of care or stay may span multiple claims, depending on the type of facility, or may be contained in one claim.

The inpatient PPS hospital claims, for instance, generally gives the episodes of care directly in one claim. The start-end dates are reliable and the stays usually last less than a month. The skilled nursing facility (SNF) and hospice claims are mainly monthly, with the stays sometimes lasting several months. These claims get concatenated by start dates and end dates in order to obtain episodes of care. Home health agency (HHA) services typically occur on a day-to-day basis. A claim from an HHA for a month lists the days on which the service call to the client's home was made. The claims are then split into the dates of service.

Once service dates for HHA visits and the episodes of care for all other facilities are determined, all of the data are sequenced by start and end dates. Adjustments to the sequences were made in order to account for overlaps due to incorrectly entered dates in the data or client transfers, the latter occurring in hospice visits.

The hospice claims sometimes overlapped a hospital visit, meaning a client might have spent some time in a hospital for an illness unrelated to his/her hospice illness. The hospice claims do not reflect this transition of facility and the information will have to be deduced from a hospital claim that was submitted during the hospice stay, based on the dates. The hospice episodes are therefore then split in order to reflect this transition with a hospital episode introduced in the middle. The resulting transition would then be from a hospice to a hospital and back to the hospice.

Once the claims from all facility types are collected, sorted by client and date, and adjusted, the HHA visits that occurred between other facility visits are concatenated to form HHA episodes of care, with a start and end date, reflecting the first and last home visit between the other facility episodes of care.

The second general step is to obtain the states for the clients from the data. The definition of a state varies based on the transition sequence under consideration. For the case of facility transitions, the state would be the type of facility visited by the client (SNF, HHA, hospital, hospice, etc.). The state is obtained from the claims that constitute an episode of care for the client. Hence, if the episode of care is obtained for a facility which is a skilled nursing facility, the state would be SNF. If the client is not in any of the facilities under consideration, he or she is the default state of "home." More generally, a state can be a function of any number of attributes from the claims data. For example, a state can be a combination of the facility ID and service code. This allows for a very flexible and robust definition of states.

If the transition sequence is of procedures, meaning if we are considering the sequence of procedures performed on the client, the state would be the individual code category, e.g. the actual value of the DRG, MDC, HCPCS or other service & device coding system. If illnesses are to be the states, then states are identified by diagnosis codes in the claims.

The third preparatory step defines "spells". A client's overall sequence as derived above may contain a single spell or many spells. Here a spell serves to delineate a sequence into meaningful periods for comparison with peers. The spell, therefore is a chronological collection of states. For the facility sequence, the definition of spell that is used is based on Medicare's definition. Here a spell commences with a stay at a facility and ends when the client had been out of a facility for 60 consecutive days. If the client is subsequently readmitted, a new spell commences. This definition is used by Medicare to set coinsurance and payment limits. However, underneath it is a loose assumption that after 60 days out a facility a client is "well" once more. Each spell of the client here therefore captures a period of sickness. The definition of a spell varies depending on the type of transition sequence. Other transition sequences are discussed later in the section.

Here is an example of the setting up of states for a client, where the sequence is the transition of the client from one facility to another.

EXAMPLE 1

Setting Up the Sequence of States for Facility Visits

The states are compiled from the client's claims for the whole year. The table below gives a list of some of the possible states for the client.

TABLE 1

| State | Description |
|---|---|
| inpnn | Inpatient PPS (prospective payment system) hospital. The nn numbers refer to the MDC (major disease category) code for the client's stay at an inpatient PPS hospital (inp). For the transition sequence one may replace the 'inp' simply by this MDC code in order to base the transition on the illness, or utilize the MDC code directly. |
| Ipp | Inpatient non-PPS hospital |
| Snf | Skilled nursing facility |
| Hha | Home health agency |
| Hos | Hospice |
| hnn | Home. (the nn refers to the number of time the client has been discharged from a facility to default state of home in the spell under consideration. For every new spell the nn begins with 00. For e.g. h03 would mean that the client has been discharged from a facility to home 3 times in the spell. NOTE: This method of incrementing the discharges by a number only applies to the facility-days sequence metric described below.) |
| Ddd | Deceased |

Based on the above table, an example of a client sequence could be:

h00-inp11-ipp-h01-h00-inp01-snf-hha-h01.

In this example the client has been in a PPS hospital twice, once for MDC 11 and once for MDC 01, in a non-PPS hospital, a SNF and an HHA. The client had also been out of the non-PPS hospital for over 60 days, in the interim, meaning he had two "spells", the first one being h00-inp11-ipp-h01-h00 and the second being h00-inp01-snf-hha-h01. Note the transition from h01-h00 at the end of the first spell and the beginning of the second spell marked by h00 transitioning to 01. Note also that the client has a state of h01, meaning he has been discharged once to home in each spell.

Let us now consider other possible transition sequences and the methodology of setting up states for these sequences. As we mentioned earlier, any successive sequence of states for a client, where a chronology may be established, can be analyzed by the sequencing model. This could refer to, among others, a sequence of procedures for an illness, a sequence of drugs administered for an illness, a sequence of resources utilized by the client at a SNF, or the sequence of physician specialties visited by a client during an illness. Without loss of generality, we refer to medical procedures, drugs, prescriptions, medical devices, utilization of resources, laboratory tests, and the like as "procedures" or "treatments."

For the case where the sequence of procedures performed on the client is analyzed, the states are the procedure codes. These are obtained directly from the claims data and sorted as described earlier for the facilities. In this case no overlap adjustments are needed and no episodes need to be determined. The spell, in this scenario could be the period of illness delineated perhaps by long gaps between visits or a grouping of diagnosis codes that pertain to an illness for which the client has visited the doctor and had these procedures performed on him. For this transition sequence, we profile the doctor or alternatively the procedure code or group. In the latter case we can identify procedure codes or groups that tend to have clients with aberrant sequences.

Another example of a transition sequence is the RUGs (Resource Utilization Groups) performed on a client a skilled nursing facility. When a client stays at a PPS SNF for a period of time, the SNF will bill Medicare for the resources spent on the client. These are billed in the form of RUGs that have varying reimbursement rates. While a client may have one or more RUGs in one stay at the SNF, the SNF may only bill Medicare one RUG at a time. These RUGs may last for one or several days and a sequence of RUGs may be expected based on the client's recovery rate. In order to analyze the sequence of RUGS for aberrance, the states here are the RUGs (or higher level groupings of the RUGs), while the spell is the stay at the SNF.

One only needs to use claims from SNFs for this analysis, as only SNFs may bill RUGs. The claims are sequentially sorted by date for each client and then concatenated by start and end dates to obtain the episodes of care, that is, the whole stays by the client. The SNF claims typically contain all the RUGs billed for on the client with the start and end dates of the RUG usage. The SNF claims are then disaggregated into lines, one for each RUG with the start and end date chronologically ordered. The sequence is then set up with the RUG codes being the states. The spells are the various episodes of care. Thus, if the client visited a SNF three times in a year, staying two months at a time (episode of care is two months) with gaps in between visits, he will have three spells.

Once the sequences are set up, they are stored in a data structure in system database 500 or in working memory that lists the states in chronological order for each client. Each state is accompanied by the identification of the provider or facility responsible for the state (e.g., the identification number of the facility that the client visited, the physician that performed the procedure etc.), start and end date, insurance payment amount, type of illness (e.g., diagnosis code, MDC code) and other relevant information as necessary for computation of the transition sequence, such as physician specialty etc.

The next step is the computation of the transition metrics.

B. Transition Metric Computation

There are many metrics that may be computed using the transition sequences for the clients. These metrics desirably capture the rareness of occurrence the client's overall sequence across all state transitions. Other metrics are computed at the profiled entity level within each client sequence and across all clients that interact with the entity.

We will first look at the metrics that are computed across all state transitions and the generation of the underlying sequence probability models.

i) Metrics Computed Across all State Transitions

A first metric that captures the rareness of a sequence is obtained through a data-driven Markov model. In the Markov method, every state transition that is possible as evidenced by the data, is taken into account, and the probability of transition from every state to every other state is computed. For any state transition, say State 1 to State 2, this is done by simply dividing the number of occurrences in the data, of transition from State 1 to State 2, by the total number of occurrences of transition from State 1 to any state. Once this is done for all the possible state transitions, a look-up table (transition probability matrix) is established that contains all state transition probabilities. There are many possible Markov-type transition metrics that may be derived, each warranting a separate look-up table.

Some examples of the Markov-type sequence metrics are given below.

a) Overall state transition probability—this probability accounts for transitions from one state to another, regardless of length of stay at any state. Examples of this would be the probability of transitions from one facility type to another, such as inp-snf-hha for facility transitions, inp01-snf-inp02 for facility transitions including the illness (MDC for the inpatient stay, RUG1-RUG2-RUG3 for a stay at a snf involving three RUGs, orthopedist-cardiologist-optometrist for transition between various types of physicians.

The look-up table for this metric may be derived as follows. In the facility transition example, for each state, such as inp find the total number of discharges to any state. For the inp-snf transition, compute the number of discharges from inp to snf. The latter divided by the former gives the probability of inp-snf transition. The process may be repeated for all facility types. Similar computations may be done for any of the above state transition sequences.

b) State-days transitions including information regarding the length of stay in each state. Here, in the data processing operation, day-state is separately coded as state in the state sequence. For example: inp-inp-inp-h01-h01-h01-h01-snf-snf-snf-h02-h02-h02 . . . etc. for facility transitions. In this example, the length of stay in each state is thus taken into account (3 days at the PPS inpatient, 4 days at home and then 3 days at the snf followed by 3 days at home etc.).

The transition probabilities computed here may only apply to transitions where a time duration is applicable to each state. In the case of the facility transitions, the length of stay, that is the duration of the episode of care is used. For some transition sequences, such as procedure code sequences, the metric may not apply since a procedure is not something that a client is "in" for a number of days.

The look-up table for this transition metric is computed as follows. The sequence for the client is expanded to include the length of the episode of care. If the sequence is inp-snf-inp, and the client stayed for 3 days at the first inp, two days at the snf and five days at the second inp, the sequence is expanded to read inp-inp-inp-snf-snf-inp-inp-inp-inp-inp. If the complete period for the sequence is one year, then the sequence will contain 365 states, one for each day of the year. The transition probabilities are computed as before, finding all the transitions from inp for the denominator and all the transitions to snf from inp for the numerator, in the case of the inp-snf transition probability, and so on.

c) Conditional state transitions—these are transitions from one set of states to another set of states, and thus account for the history of the states prior to the transition point of interest. More generally, this is the transition probability for a transition between a sequence of states (A, B, C . . . ) to another sequence of state (D, E . . . ). In the special case of each sequence having just one state, this is simply the state transition probability described above. In the case where the origin sequence includes two or more states, and the destination sequence includes at least one, then this reflects the conditional probability. For example, the transition from the sequence (inp-snf) to inp, the transition metric describes the probability of a transition from the snf to the inp given that the client was an inpatient prior to the snf.

These metrics are second order probabilities, as they take into account the state prior to the current state of the beneficiary. A simple way to compute this metric would be to look at transition from facility pairs. For example, in the sequence inp-snf-inp, we would look at the transition from the pair (inp-snf) to inp. The denominator in this case will be transitions in the data from the (inp-snf) pair to all facility types. The numerator would be the count of transitions from the (inp-snf) pair to inp. A look-up table is generated that contains all possible transitions present in the data.

These are examples of certain metrics that capture the rareness of the sequence. There are other metrics that may be used to achieve a similar result.

These look-up tables provide a norm for the transitions as determined by the population. If a certain transition has a high probability, then it implies that according to the population that particular transition is fairly common. Conversely a low transition probability implies a rarely occurring transition. For instance, the transition probability of going from a hysterectomy procedure to a delivery would not be very high in the data, while the probability of going from cardiac surgery to rehab would be high.

Once the look-up tables are generated, the rareness of every beneficiary spell may be computed. One way to do this would be to find the product of the transition probabilities of every transition in the sequence for the spell. For example, if the sequence is inp-snf-inp, the sequence probability would be the product of the inp-snf transition and the snf-inp transition.

The overall sequence probability can be developed along the multiplicative approach by simply using the geometric mean of all the probabilities, which then provides a fairer comparison between longer and shorter sequence. (A longer sequence will generally tend to have a lower transition probability than a shorter one.) The overall transition probability will give an indication of the rareness of the sequence. If the transition probability is low then the sequence on the whole has many rare transitions within it. The rareness of every client spell in the data for the all the various types of transition metrics is computed. The result is a table of rareness metrics for the client spells, where a client may have multiple metrics, one for each spell.

In addition to metrics that capture the rareness of a sequence, certain metrics may be calculated from the sequence that give an idea of the characteristics of the sequence. These are metrics such as number of states visited, average lengths of stay at the states, if applicable, and the number of states of each type, if there are more than one type of a state (e.g., inp, snf etc.).

The metrics computed so far are at the client spell level. These metrics can be usefully "rolled up" to the entities being profiled. If the entity being profiled is the client, then the metrics from the multiple client spells will be rolled up to the client. If the level is higher, such as the facilities the client visits or the doctors the client sees, then the rollup is typically done to all the elements of the entities visited by the client, i.e. all the facilities visited, all the physicians, all of the pharmacies visited etc. The idea is to identify entities that interact with a preponderance of clients with rare metrics. Thus, if client P has visited four facilities during a spell and six doctors, there would be individual rollups for each of these ten entities.

One of the methods of roll up is described below. Once the entities that interact with the client are determined, say the facilities or doctors, then a table is generated that contains a list of all the metrics from the client spell level, of all the client spells for all clients that were treated by the particular entity. From this list, which is in essence a distribution of metrics for the profiled entity, quantities that capture the distribution such as the mean, standard deviation, etc. may be calculated. These are then variables at the profiled entity level to use in the model. An example of a variable in the profile of a facility is the average facility-day transition probability for the facility, where the sequence metric is the state-day transition probability described earlier (the state being a facility-date) and the roll-up is done across all the client spells that intersected with this facility. More details of how rollups are computed for entities is described in the Cascaded Profiles application cross-referenced above.

Here are some other examples of roll-ups. If we are looking for clients committing fraud, then the roll-up is done to the client level, from the client spell level. For example, we can determine for each client the average transition probabilities across all spells of the client. Investigation may be done on the clients with lowest transition probabilities.

If we are looking for doctors committing fraud in conjunction with specific clients, we would roll up to the doctor-client level. This would essentially mean finding all the transition metrics at the client spell level for clients that visited the specific doctors and calculating roll-up metrics for these doctors such as averages, and finding aberrant doctor-client pairs.

We might also be interested in looking at overall impact on the insurance industry by certain procedures, for instance. In this case, the profiled entity is the procedure, which is also the state in the transition sequence. This would involve finding the client spell metrics and then rolling them up to the state, i.e. the procedure. The insurance industry might Want to look at procedures that have a preponderance of clients with low transition probabilities.

Thus, the roll-up method depends on the entity being profiled. The basic purpose of the model is to sequence a set of occurrences, where a sequence is relevant, and look at aberrance by going through the object undergoing the sequence and/or at a higher level, such as the state or another entity being profiled.

ii) Metrics Computed with Additional Constraints

We will now discuss the metrics that are computed directly at the level of the entity being profiled, which do not need to be rolled up. These metrics are also transition metrics, but are computed from transitions of clients from or to states that pertain directly to the profiled entity and not across all the states that the client visits. These metrics are similar to the transition probability metrics computed earlier but have additional conditions and constraints imposed on them, the primary constraint generally being that the state occurs at the profiled entity. All of the metric examples described below, in this section, have a degree of specificity relating to the particular type of state transition sequence being analyzed. However, many of them may be generalized and used in any other types of transition sequences.

As mentioned earlier, these metrics may be defined and calculated directly at the profiled entity level. (In a sense, though, these are actually first calculated at the profiled entity-client spell level and then rolled up immediately through summation to the profiled entity.). These metrics, therefore do not need to be rolled up further. The transition probability derived here in these metrics is specific to the profiled entity in question. A high or low probability does not indicate commonness or rareness as was the case when the probability was calculated across the population. So if transition probability for a particular sequence such as inp-snf-inp is low for a facility, it may not necessarily be rare and the rareness can be determined only when comparing this metric to the norm for all facilities of the same type. For example, if the mean and standard deviation of this probability is calculated for all the facilities of same type and the lower the probability is than the mean, in units of standard deviations, the greater is the rareness of the transition for that facility. In that sense, while these metrics are derived emphasizing known fraud patterns in many cases, the aberrance of these metrics from the norm, which may signify fraud or abuse, or likewise, their direct indication to fraud or abuse are evaluated through either the predictive model 4 or the rules based analysis 5 with the appropriate filtering rules based on the value of the transition metric. Here are a set of examples describing the derivation and usage of these metrics.

EXAMPLE 1

There are situations where facilities rotate clients in certain patterns. An example is in prospective payment system hospitals where payments are made in fixed amounts and not on a per diem basis. Here the hospital may discharge the client or send her to less expensive facilities. If the clients are not well enough to be discharged, they may end up being readmitted to the hospital which is an indicator of poor quality of care, and hence an abuse of the payment system. Some of these metrics, therefore, characterize specific chains such as inp-snf-inp, inp-hha-inp or inp-ipp-inp etc., where the client moves from the hospital to another facility and back to the hospital. Say we are looking at the problem of facility transitions by clients and are interested in the inp-snf-inp sequence, but the first 'inp' refers specifically to facility XYZ, one of the entities being profiled and not all inpatient facilities in general. The second 'inp' could be any inpatient facility. In this case, the transition probability will be derived by finding not all discharges from all 'inp's but only discharges from 'inp' states that occurred at facility XYZ. The denominator is then the count of all discharges from facility XYZ to 'snf's. The numerator would then be the count of all transitions from 'snf' to 'inp', where the 'snf' in question was from a discharge from facility XYZ. More specifically:

$$P(XYZ\text{-}snf\text{-}inp)=F(snf\text{-}inp, \text{assuming } XYZ\text{-}snf)/F(XYZ\text{-}snf).$$

A variation on this metric would be to impose the additional constraint that the readmitted inpatient facility be the original discharging facility XYZ. This concept of mini-sequences can also be extended to other state types, such as procedure codes etc. depending on the transition sequence being considered.

EXAMPLE 2

Another such metric would be the computation of readmission probability to a facility within a specified time, say 7 days. If clients that are discharged from a facility are readmitted within a few days to the facility and this happened at a fairly high rate, as shown by a relatively high transition probability for the facility, then this may indicate that the discharged clients are not well enough to be discharged in the first place. The metric is calculated in much the same manner as above where the transition probability of the inp-inp sequence is computed, where both the 'inp' states pertain to facility XYZ with the condition that the transition happen within 7 days of discharge.

EXAMPLE 3

Yet another example would be the admission of clients to a SNF. A SNF is typically a less expensive facility than a hospital and also provides less intensive care. An admission to a SNF requires a minimum qualifying stay of three days at a hospital prior to the admission. If hospitals are keeping clients just long enough to meet the qualifying rule prior to discharge to a SNF, this may indicate poor quality of care, especially if done at a great rate. Computation of this metric would involve again the inp-snf transition probability as before, but with different constraints. The denominator would be the total number of discharges from inp facility XYZ to a SNF, and the numerator would be the number of these discharges that had an exactly three day stay at the 'inp' state. The data processing operations for creating the sequences are readily adjusted to identify these sequences.

EXAMPLE 4

Here is an example of a metric computed at the profiled entity level where the profiled entity can be a doctor performing procedures on clients. Let us say we are interested in sequence (procedure 1-procedure 2), where we want to find the probability of procedure 2 happening after procedure 1 within a span of a few days. If the profiled entity is the doctor then we find the number of the doctor's clients that underwent procedure 1 and of those, the ones that also underwent procedure 2 within the specified time. This is a conditional transitional probability. (Note: If the profiled entity is the procedure code, then the transition probability in this case could be obtained directly from the look-up table calculated earlier, which is the transition probability from procedure 1 to procedure 2.)

EXAMPLE 5

Yet another example is the transition probability of the inp-snf chain from the 'inp' facility XYZ, for transitions that happen from this facility to only 'snf' or 'hha'. This is the proportion of clients discharged from the facility XYZ to a SNF, among all the clients that were discharged from this facility to either SNFs or HHAs.

Although the examples shown above are for facility-to-facility transitions by clients, this type of metric definition and computation may easily be extended to other types of state transitions such as a physician specialty sequence, like an orthopedist-chiropractor-orthopedist sequence, or procedure code sequences, among others.

In summary, many such metrics may be computed at the profiled entity level. It must be emphasized that these metrics are similar to the transition probability metrics derived earlier, except with the additional constraint that the states intersect with the profiled entity and other constraints, including and not limited to temporal ones, such as those that dictate some measure of time occurring between transitions or spent at a state. Generalizing the above, we can say that constrained metrics are those where a transition probability is computed for a sequence S, the sequence including states s1 through sn, where a constraint is placed at one at one of the states, the constraint being one or more of the following:

one or more states are defined to be a particular instance (e.g., a particular procedure, facility, doctor, facility-service code combination, facility-date, etc.);

one or more states are defined to be of a type (e.g., a snf or a general procedure category);

the transition between states or the duration of stay at a state has temporal restrictions.

Figure 3:
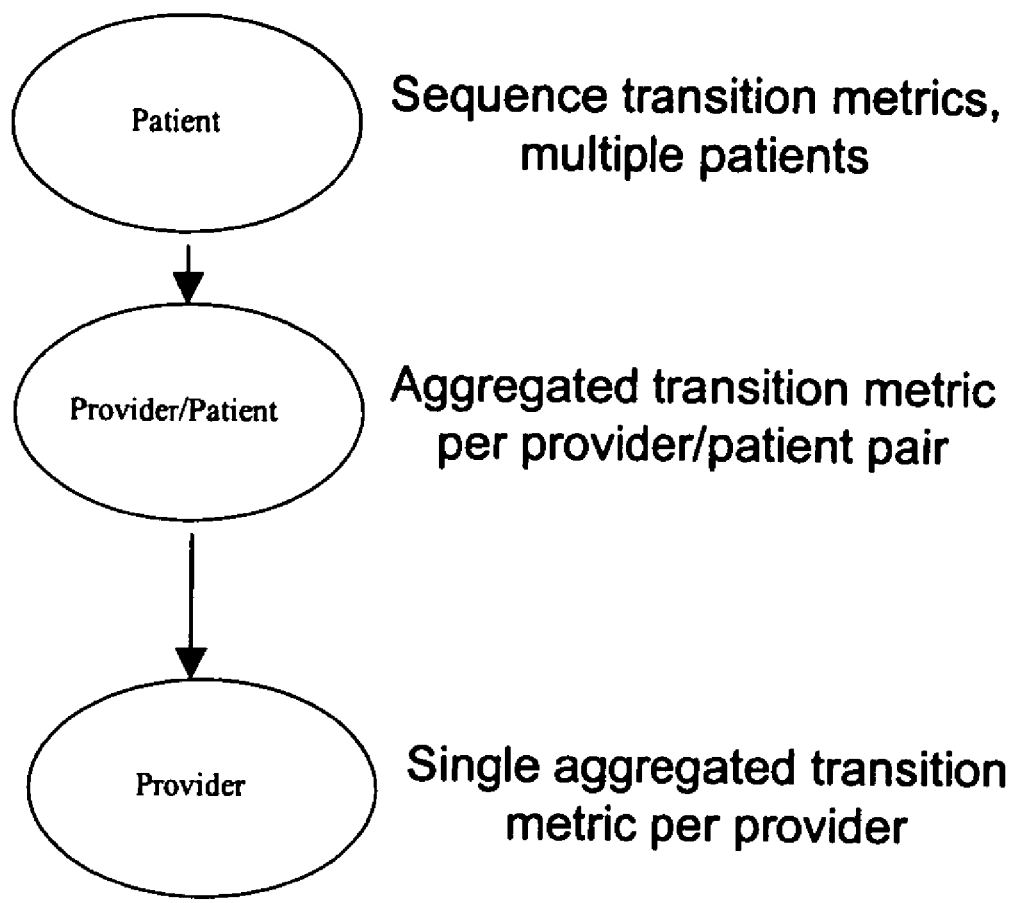
FIG. 3 is a flowgraph of the profile rollup process.

At this point we have a set of metrics at the profiled entity level, some rolled up from the client spell level and others directly computed at the profiled entity level. The cascaded flow diagram in FIG. 3, illustrates this rollup mechanism, where the profiled entity is a provider, such as a doctor or facility. The methodology for "rolling up" metrics of multiple different entities is described in detail in the Cascaded Profiles application, as mentioned above. As an example of the roll-up in the context of FIG. 3 is as follows. At the patient level, sequence transition metrics are determined across multiple patients; at the provider/patient level, the aggregated transition metric per provider/patient pair is determined (i.e. merge operation for all patients associated to an individual provider); finally at the provider level, single aggregated transition metric per provider is determined (e.g., minimum over all patients of the geometric mean).

The next step is to create an underlying model. The model involves first collecting all the variables for the profiled entities, generated either through roll ups or computed directly at the profiled entity level. These profiled entities are then compared to their peers and certain parameters are extracted that will give an indication of aberrant or fraudulent behavior of the profiled entities, leading to a score and a rank-ordered list of profiled entities by descending degree of aberrance. The use of predictive models to score profiled entities for aberrance is disclosed, for example, in U.S. Pat. No. 5,819,226, which is incorporated by reference herein.

III. Exemplary Implementation

We now turn to a discussion of a specific computational architecture for determining transition metrics. Reference is made generally to FIG. 2. The initial process 3001 is to ensure that claims become keyed on date-of-service (DOS) for each of the entities being followed; thus process 3001 segregates a set of claims by entity, and then for each entity sorts the claims by date of service. The entity of interest is usually the client as previously mentioned, but it could be represented by another entity.

Once the claims are properly ordered, the state process 3002 will then closely follow specific operational definitions in determining the states being modeled in preparation of the sequence information. The definitions, provided by a system monitor, define what fields, attributes or other aspects of a claim are to be identified as indicative of a state. The various examples described above for states are illustrative. States can be identified at different levels according to a state hierarchy process 3002B. For example, as previously discussed for the hospital inpatient setting, the category of treatment/condition combination of a client could be tracked at the fairly high level of the DRG or even at the even coarser level of the MDC. This hierarchy process thus permits the flexibility of having states at various levels of bundling or unbundling. The result of this step is a set of state sequences, each sequence associated with an entity and having one or more specific states.

In establishing such series of consecutive states, some definitions may cause overlap in two or more states, thereby confusing the exact nature of the individual state of the client at a given time point. If such overlaps do occur, filtering process 3002A will resolve them and thus produce a clean suite of distinct states. A simple filter simply follows a precedence rule of states, e.g. if a hospice state and hospital state overlap, then assign the claim to the hospital state. This type of filtering rule generally selects the more significant state from two or more overlapping states; significance can be based on average costs associated with various states, length of stay in a state, or other operational factors selected by the system designer.

Once the set of state sequences has been extracted from the claims, the transition process 3003 calculates the observed value of the transition metrics, such as distributional characteristics or transition probabilities. Distributional characteristics could include:

the number of states visited;

the frequency count for each specific state;

the average length of stay for each state;

the mean, standard deviation (or percentile) number of states in a sequence;

the frequency count for each state transition (from state A to state B);

the total number of state transitions regardless of state;

The transitional probabilities are represented by first- or higher-order transitional probabilities accumulated all the states visited by the client. First-order transition probabilities capture the proportion of transitions from one individual state to another across all possible transitions with the same initial state. For example, the state transition probability P for the transition from state A to state B is:

$$\text{Prob}(A,B)=\text{Freq}(A,B)/[\text{Freq}(A)]$$

Where Freq(X,Y) is the frequency of transitions from state X to state Y, and Freq(X) is the total number of transitions from state X to all other states.

Higher order transition probabilities instead look at the relative frequency of transitions between sequences of two or more states. For example, we can define a transition probability from the sequence of states {A,D} to state C, by first counting the number of transitions from sequence {A,D} to state C, that is Freq({A,D},C), and dividing by Freq({A,D},X}), where Freq({A,D}) is summed over all possible states X. A higher-order transition could also start with a single state and end with a sequence of states, e.g., (A, {C,D,E}). More elaborate versions of the higher order transitions can also be developed by induction, i.e. going from a sequence of more than two states and-or going to a sequence of more than two states, e.g. transitions from a long sequence to another long sequence as ((A, B, C, D, . . . ), (W, X, Y, Z, . . . )). The resulting metrics are conveniently stored in lookup tables 300.

For transitions realized by (or to) a client, an individual client's sequence metrics consist of summary functions of each of the transition's assigned probability norm (obtained from the lookup tables 300). The most common function would be the rareness metric, i.e. the observed geometric mean of the transition probability norms (from tables 300). The transitional probability norms need to be calculated at least once and can be updated as necessary (yearly, quarterly, or even monthly should prove sufficient) by the update process 3A. Update process 3A operates on initial, or additionally received, claims by passing those claims through the DOS key process 3001 and state process 3002 to create the sequences. Once the sequences are ready, each transition pair's frequency is tabulated to yield the transitional probability norms. These probability norms can be global (without population segmentation), or peer-specific under different approaches, such as disease-specific, by client categories, by geographical regions, etc. or combinations of such approaches. A separate transition probability norm table is used for every state hierarchical level.

Process 3003A calculates additional state and transition metrics that incorporate supplementary characterization of the states or transitions, such as the time spent in a particular state before or after a transition (based on the dates of service associated with each state), and/or the narrow focus on particular states or transitions, with other additional constraints. For example, the client readmission rate is a significant feature of quality-of-care for certain facility and/or disease types. A specific example is this: the usual state transitions for CHF (congestive heart failure) readmissions, as tracked by inp127-hh01-inp127, would be further constrained on whether the time spent at home was less than a month to track within-30-days readmits for this condition. An overabundance of such rapid readmits combined with considerably shorter inpatient stays would warrant serious scrutiny by utilization review. Also, regulations require some facilities to only admit clients after a proper qualifying stay at another facility (such as the previously mentioned example of the qualifying inpatient hospital stay for SNFs). Repeated violations of such regulations would prompt immediate compliance audits and/or investigations.

Once all the metrics are calculated, the entity process 3004 produces the information at another entity level, such as the derive, rollup, enhance, and merge processes discussed in the "Cascaded Profiles", the cross referenced application identified above, and incorporated here. For example, all metrics can be calculated at the client level and then rolled-up at the facility level. At this point, the profiles are ready.

Profiles can be used for higher level processing, for example to build predictive models 4, get fed into scoring engines 6 (from the predictive model 4) and provide rule-based analyses 5. Model scores are best supported by explanatory reasons. The predictive model involves first collecting all the variables for the profiled entities, generated either through roll ups or computed directly at the profiled entity level. In the scoring engine, these profiled entities are then compared to their peers and parameters are extracted that will give an indication of aberrant or fraudulent behavior of the profiled entities, leading to a score and a rank-ordered list of profiled entities by descending degree of aberrance. In the context of rule-based analyses, the profiles would be fed into engines which would score the entities based on their adherence to the specified rules as indicated by the profiles.

IV. Deployment

Deployment of entity profiles and ensuing probability models in a production environment is relatively straightforward for most of the processes. The entity process 3004 requires special handling of the tracking of entities before they get combined, and in the timing of the interacting steps of the multi-entity profiling approach. The multi-entity profiling approach is referred to in the Cascading Profile application.

In a production environment, the post-score process 6 prepares supporting score reasons and an assortment of profile-related statistics and reports (at the different entity levels). All such results (scores and supportive multi-entity information) are made readily available for end-users (7), either through its own database (400) or within the system database (500).

A preferred user interface the data analysis tool described in the Webstation application cross referenced above. For real-time implementation four options can be considered:

Webstation as report tool only—pass back scores and reasons to claims flow. End-user does workflow & case management, and uses Webstation only for reports Webstation as report and workflow tool—pass back nothing to claims flow. End-user does all of the work manually.

Enhanced version of the Webstation as report and workflow tool—same as previous item but tightly integrated by passing back scores and reasons into claims flow, case management, etc.

Webstation "supreme"—ICN, status, and explanation all passed back to claims flow and/or case management. Workflow and status setting controlled by rules and can impact new and existing edits. Full control by Webstation for what is passed back into the claims system: at the claim level, but at the edit level as well. Perhaps the most appealing aspect of a real-time implementation is the opportunity for controlling the how to return (automatically or manually) rules/edits into the claim processing system.

Once the model is created and stored, it is ready to be used in the production environment. The models need to be updated as and when necessary. In the production mode, the entities to be profiled are selected and the profiling is done in a manner similar to the profiling prior to model creation. In the non-real time analysis setting, the profiling is identical to the profiling for the model, while in the real-time setting there may be some differences.

In the non-real time setting the profiling for the entities proceeds in the following manner. The claims are processed and sequenced in a manner similar to the one described above to determine episodes of care. Adjustments are made for overlaps as necessary, after episodes from various sources are collected and sorted by start and end dates. The states are determined, as well as the client spells. The transition probabilities for the client spells are then computed using the look-up table. Other metrics at the client spell level are also computed. These are the metrics that capture sequence characteristics, such as number of states, etc. The roll up is done to the level of the profiled entity. The metrics at the profiled entity level are then computed and all the variables thus generated are collected together to form the profile for the profiled entity. This set of variables, or the profile, is then passed through the model, compared to the norms and scored for aberrance. The top ranked entities typically have a preponderance of clients (or objects) with rare sequences or aberrance in the other metrics calculated for them V. Review Process and Interpretation The potential users of the outcomes of this invention (e.g., profiles, model scores and reasons, or detection from rules) would include, in the area of insurance, claim adjusters, quality (including clinical) review staff, actuaries and claim analysts, staff of special investigative units, etc.

We have discussed the interpretation of the transition metrics variously above. Some of the metrics, such as the average number of states visited by a client, or the metrics computed at the profiled entity level, such as the transition probability of a time-constrained sequence occurring at the profiled entity, have clearly understood meanings. The investigation of overall transition probability metrics that are rolled up to the profiled entity level from a lower level are more slightly more involved in their investigation. Generally, if the entities that are profiled are at the lower levels, such as the client and provider/client pair, say, we can consider the individual sequence. In this case, for example, all clients with relatively low overall transition probabilities might be worth investigating. To investigate aberrance in the sequence Markov-type metrics at the rolled-up levels, we look at all the clients for the entity being profiled especially the ones with the low transition probability metric. The investigation process will focus on entities with a preponderance of clients with rare transition sequences. In many cases the rareness of each individual client's sequence might be explainable, when considered separately, but when coupled with all other rare client sequences for the profiled entity, might indicate fraudulent or abusive behavior. So, while a client might make one or more rare transitions, and have a low overall transition probability and deeper investigation may rationalize the need for the transitions, it may be more difficult rationalize when a relatively overwhelming portion of the entity's clients engage in these aberrant transitions. Another aspect of the investigation comes from the fact that since the transitions generally involve various states, they will more likely involve various profiled entities. Thus the investigation of one suspect entity may also lead to other entity with suspicious behavior.

The present invention has been described in particular detail with respect to one possible embodiment. Those of skill in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component. For example, the particular functions of the data processing blocks, the profile derivation, or the analysis module, and so forth may be provided in more or fewer modules. Also, predictive model may be implemented in a variety of modes, including a neural network, a multivariate regression model, or any other model that classifies inputs based on statistical analysis of historical exemplars.

Some portions of above description present the feature of the present invention in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real time network operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It is appreciated that a variety of programming languages may be used to implement the teachings of the present invention as described herein, and any references to specific languages are provided for disclosure of enablement and best mode of the present invention.

The present invention is well-suited to a wide variety of computer network systems over numerous topologies. Within this field, the configuration and management of large networks comprise storage devices and computers that are communicatively coupled to dissimilar computers and storage devices over a network, such as the Internet.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

We claim:

1. A computerized method of identifying potentially fraudulent healthcare reimbursement claims, comprising:
   determining a sequence of healthcare states for a client from healthcare reimbursement claims associated with the client, wherein determining said sequence comprises:
      segregating said healthcare claims by entity;
      for each entity, sorting by date;
      responsive to sorting, determining states to be modeled, wherein said states are identified at levels based on a state hierarchy process, and wherein each sequence comprises one or more states;

storing said sequence in a data structure that lists the states in chronological order for each client, said data structure residing either in a system database or in working memory;

processing healthcare reimbursement claims for a population of clients and healthcare providers for a selected time interval to identify a total set of potential healthcare states in a collection of healthcare data;

for each individual transition between healthcare states contained in a model derived from the collection of healthcare data, determining a probability of the healthcare state transition as the ratio of the frequency count of a transition from a first state to a next state, to total count of transition for the first state to all other states in the reimbursement claims;

calculating a transition probability of the sequence of healthcare states based on probabilities of individual transitions between healthcare states as contained in said model, wherein said transition probability of the sequence is the geometric mean of the transition probabilities between each state and the next state in the sequence;

identifying the sequence as potentially fraudulent as a function of the probability of the sequence wherein said probability of sequence is distinct; and outputting a transition metric based on the transition probability of each sequence.

2. A method for identifying potentially fraudulent or abusive treatment practices by healthcare providers, comprising:

processing healthcare reimbursement claims for a population of clients and healthcare providers for a selected time interval for treatments provided by the providers to identify a total set of potential healthcare states in a collection of healthcare data and to determine transition probabilities for sequences of healthcare states for the treatments, wherein transition probabilities for sequences are determined based on probabilities of transitions between healthcare states previously calculated by determining a probability of the healthcare state transition as the ratio of the frequency count of a transition from a first state to a next state, to total count of transition for the first state to all other states in the reimbursement claims as contained in a model derived from the collection of healthcare data, and wherein said sequences of healthcare states are created by:

segregating by entity;

for each entity sorting by date;

responsive to sorting, determining states to be modeled, wherein said states are identified at levels based on a state hierarchy process, and wherein each sequence comprises one or more transitions, and wherein the transition probability for a sequence of states is the geometric mean of the transition probabilities between each state and the next state in the sequence;

for each provider, determining an aggregated transition probability for all sequences of healthcare states for treatments provided by the provider;

comparing said aggregated transition probability of each said provider with the aggregate transition probabilities of providers of similar treatments in said population of healthcare providers;

identifying as potentially fraudulent at least one provider having aggregated transition probability that is statistically different from the aggregate transition probabilities of providers in said population of healthcare providers of similar treatments; and reporting said potentially fraudulent provider.

3. The method of claim 2, wherein determining an aggregated transition probability for all sequences of healthcare states for treatment provided by the provider comprises:

for each client treated by a provider, determining a transition probability for each sequence of healthcare states including at least one treatment provided by the provider the client; and determining the aggregated transition probability for the provider as a function of the transition probabilities determined for each sequence of each client.

4. The method of claim 3, wherein:

for each pair of states, there is a transition probability for a transition between the states.

5. The method of claim 2, wherein processing healthcare reimbursement claims for treatments provided by the providers further comprises:

for each client in a population of clients, determining a transition probability for each sequence of healthcare states experienced by the client.

6. A method for creating a model of healthcare states, comprising:

processing healthcare reimbursement claims for a population of clients and healthcare providers for a selected time interval to identify a total set of potential healthcare states in a collection of healthcare data, each reimbursement claim related to a client and healthcare treatment;

for each client:

extracting from the claims related to the client a plurality of treatments;

determining at least one sequence of healthcare states from the treatments by:

segregating by entity and for each entity sorting by date;

responsive to sorting, determining states to be modeled, wherein said states are identified at levels based on a state hierarchy process, wherein each sequence comprises one or more transitions between states, and wherein each state is associated with a provider;

for each pair of states in each sequence, updating a frequency count of a transition from a first state to a next state;

for each state, determining a total count of transitions from the state to all other states based on the frequency counts;

for each state transition from a first state to a next state, determining a transition probability for the state transition as the ratio of the frequency count from the first state to the next state, to total count of transition for the first state to all other states; and after all transition probabilities are determined for each state transition, creating a look-up transition probability table that contains all state transition probabilities for subsequent transition probability in said model;

said method further profiling healthcare entities in accordance with the steps of:

processing healthcare reimbursement claims for a population of clients and healthcare providers for a selected time interval to identify a total set of potential healthcare states in a collection of healthcare data;

determining at least one sequence of healthcare states from healthcare reimbursement claims associated with an entity by segregating by entity and for each entity sorting by date, then, responsive to sorting, determining states to be modeled, wherein said states are identified at levels based on a state hierarchy process, wherein each sequence comprises one or more transitions between states, and wherein a sequence of healthcare states represents client experiences in one or more episodes of care;

for each individual transition between healthcare states contained in a model derived from the collection of healthcare data, determining a probability of the healthcare state transition as the ratio of the frequency count of a transition from a first state to a next state, to total count of transition for the first state to all other states in the reimbursement claims;

determining a transition probability of each sequence based on transition probabilities of transitions between healthcare states, wherein a previously determined transition probability of an individual healthcare state is determined using the said look-up table, and wherein the transition probability for a sequence of states is the geometric mean of the transition probabilities between each state and the next state in the sequence; and generating a profile of the entity that includes a transition metric based on the transition probability of each sequence.

7. The method of any of one of claims 1, 2 or 6, wherein the healthcare states are facilities providing procedures to clients.

8. The method of any of one of claims 1, 2 or 6, wherein the healthcare states are services codes for healthcare procedures.

9. The method of any of one of claims 1, 2 or 6, wherein the healthcare states are the healthcare providers.

10. The method of any of one of claims 1, 2 or 6, wherein the healthcare states are provider-days.

11. The method of any of one of claims 1, 2 or 6, wherein the healthcare states are provider-service codes.

12. A system for creating models of healthcare claims, comprising:

a database of healthcare claims, each claim including identification of a client, a provider, at least one procedure, and a date, wherein healthcare reimbursement claims are processed for a population of clients and healthcare providers for a selected time interval to identify a total set of potential healthcare states in a collection of healthcare data;

a data processing module that processes a set of the claims into date-ordered, entity specific sequences of states by segregating by entity and for each entity sorting by date, then, responsive to sorting, determining states to be modeled, wherein said states are identified at levels based on a state hierarchy process, wherein each sequence comprises one or more transitions between states, and wherein a state comprises any of: facilities providing procedures to clients, services codes for healthcare procedures, healthcare providers, provider-days, and provider-service codes;

a transition processing module that determines, from the date ordered entity specific sequences, a transition metric for each transition between states, wherein said transition metric for each transition between states is based on the ratio of the frequency count of a transition from a first state to a next state, to total count of transitions for the first state to all other states in the reimbursement claims; and an entity profiling module that generates profiles for at least one entity and a transition metric for one or more sequences of states related to the entity, wherein said transition metric for a sequence of states is the geometric mean of the transition probabilities between each state and the next state in the sequence.

13. The system of claim 12, further comprising:

an analytical module that receives the profiles and identifies entities that are potentially fraudulent or abusive based at least in part upon the transition metrics contained in the profiles.

14. The system of claim 13, wherein the analytical module includes a predictive model.

15. The system of claim 13, wherein the analytical module includes a rules based model.

16. The system of claim 12, wherein an entity is one of the group consisting of:

a client;

a healthcare provider;

a provider/client; and a procedure.

* * * * *